US012611309B2

(12) United States Patent
Semenescu et al.

(10) Patent No.: US 12,611,309 B2
(45) Date of Patent: Apr. 28, 2026

(54) SHORT IMPLANTED PROSTHESIS AND METHOD OF MAKING SAME

(71) Applicants: Augustin Semenescu, Buchare (RO);
Ruxandra Vidu, Citrus Heights, CA
(US); Ileana Mates, Buchare (RO)

(72) Inventors: Augustin Semenescu, Buchare (RO);
Ruxandra Vidu, Citrus Heights, CA
(US); Ileana Mates, Buchare (RO)

( * ) Notice: Subject to any disclaimer, the term of this
patent is extended or adjusted under 35
U.S.C. 154(b) by 433 days.

(21) Appl. No.: 18/144,229

(22) Filed: May 7, 2023

(65) Prior Publication Data

US 2024/0366391 A1       Nov. 7, 2024

(51) Int. Cl.
A61F 2/36 (2006.01)
(52) U.S. Cl.
CPC ............ A61F 2/367 (2013.01); A61F 2/3676
(2013.01); *A61F 2002/3631* (2013.01); *A61F*
*2310/00023* (2013.01)
(58) Field of Classification Search
CPC .......... A61F 2/36; A61F 2/367; A61F 2/3676;
A61F 2002/3631; A61F 2002/3625; A61F
2002/3652; A61F 2310/00023
See application file for complete search history.

(56) References Cited

U.S. PATENT DOCUMENTS

2002/0138151 A1*   9/2002   Hubbard ............... A61F 2/3662
623/23.35
2012/0095568 A1*   4/2012   Grappiolo ............. A61F 2/3662
623/23.26

* cited by examiner

*Primary Examiner* — Vi X Nguyen

(57) ABSTRACT

An implanted prosthesis for orthopedic and dentistry sur-
geries having a short body implant and an internal channel
having an arborization system of orifices for delivery the
necessary osteo-forming substances is disclosed. The
implanted prosthesis can be created by additive manufac-
turing and includes a short body portion having a helicoid on
the exterior wall, a collar, a neck, which are all aligned on
the longitudinal axis of the prosthesis. The prosthesis neck
has a hexagonal orifice for the insertion of dynamometric
screwdriver to fix prosthesis in place. The hexagonal orifice
communicates inside the body with a cylindrical orifice of
variable length and diameter, which further communicates
with the arborization system of orifices that provide lateral
feed with cement and osteo-forming substances, and anchor-
ing. In the middle of the central chamber there is a small
threaded area in which a syringe to introduce cement or a
threaded cap can be screwed.

2 Claims, 8 Drawing Sheets

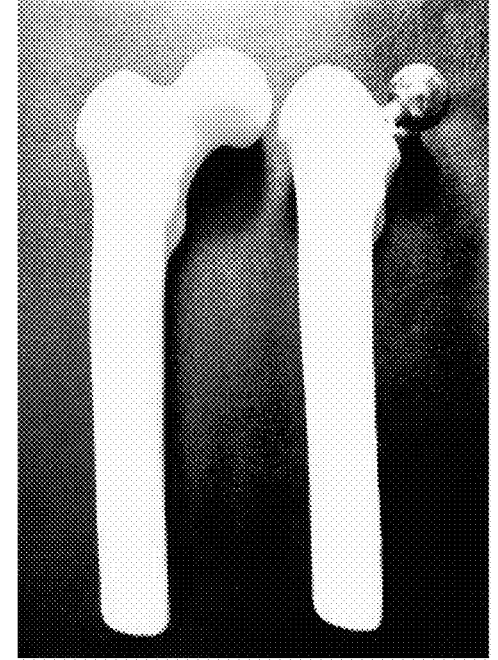
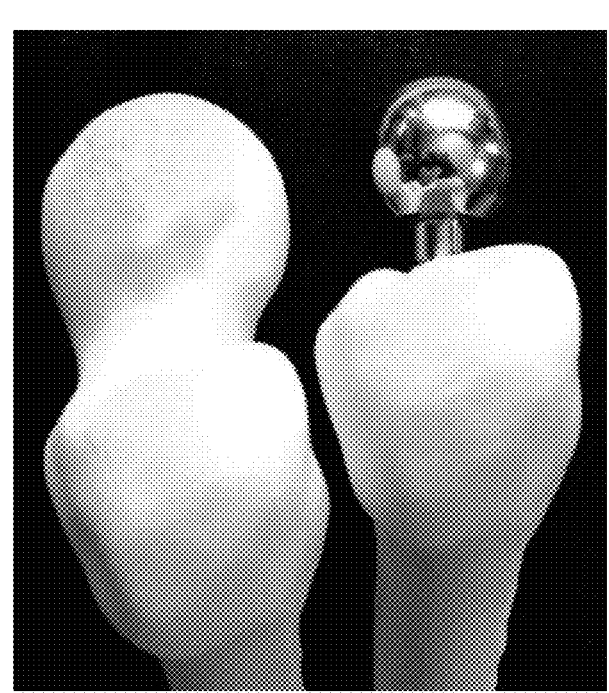
FIG. 8                              FIG. 9

SHORT IMPLANTED PROSTHESIS AND METHOD OF MAKING SAME

STATEMENT REGARDING FEDERALLY SPONSORED RESEARCH OR DEVELOPMENT

Not Applicable

BACKGROUND OF THE INVENTION

The length of an implant is an essential factor in determining the overall success of the prosthesis. Worldwide in implantology in general, and also in the complementary fields, numerous theoretical and applicative studies focus on designing and making new implants, prostheses, external fixing devices and instruments necessary for surgical interventions, as well as new surgical techniques.

In the case of cervical femoral endoprosthesis, the current practices involve an almost complete resection of the femoral neck followed by the prosthesis insertion up to the medullary canal using brute force. For instance, in the patent US20150025649 A1, a hip prosthesis to be introduced in a femur is presented. The hip prosthesis has a close end adjacent to a hip articulation, a distal end adjacent to the knee articulation, an anterior part, a posterior part, a middle part, a lateral part and the medullary canal, the prosthesis comprising the following: a stem with a proximal end, a distal end and a longitudinal axis between these, the stem including an anterior blocking surface and posterior blocking surface, these surfaces each being differently oriented with respect to the stem axis, at an angle higher than 3 degrees, the stem also including a tail portion extending adjacently with respect to the anterior and posterior blocking surfaces. The stem portion converges angularly with respect to the stem axis and one of its necks extends in an angle from the proximal end of the stem.

In the patent RO117890, a femoral component of a total hip prosthesis that replaces a natural coxofemoral jointing is presented and which, for the purpose of using certain accessible biocompatible materials and for increasing the total prosthesis reliability, consists of a body that has a flat elongated shape having a "handgun" configuration, the distal part being continued in a "dovetail" that follows the anatomic structure of the femur metaphyseal area.

A partial hip prosthesis or short-stem total hip arthroplasty replaces the damaged cartilage of the hip joint bone restoring only the part affected by the disease, preserving most of the bone and leaving the rest of the femur bone in place. Through the prosthesis, the femoral neck anatomy, the length of the femoral neck and its orientation or anteversion is preserved, achieving a complete restoration of the function of the injured hip as it was before the onset of the disease. These implants are designed to restore the function of the hip joint affected by osteoarthritis, fractures or tumor formations, especially the benign ones. If the femur, i.e. the thigh bone, is still viable and stable, it will be preserved and only the damaged head of the femur is replaced with an artificial femoral head, along with the acetabular cavity (i.e., the acetabular cup with the appropriate attachment corresponding to the prosthetic head).

BRIEF SUMMARY OF THE INVENTION

Because the choice of the length of an implant is a vital factor in controlling the overall success of the prosthesis in many surgeries and decreasing the implant failures, the present invention applies to many implanted prostheses used in common orthopedic and dentistry surgeries, prostheses that have a short body implant and a need to deliver the required osteo-forming substances through an interior channel having an arborization system of orifices.

The present invention describes in detail a short implanted prosthesis that consists of an interior chamber for delivering and controlling the substances required for fixing and healing the prosthesis. A part of the distal end of the prosthesis has a helicoidal spiral on the exterior wall of the cylindrical body to promote the prosthesis insertion. This type of short implant is created using additive manufacturing due to its complex geometry. As the name suggests, additive manufacturing adds material to create an object. Additive manufacturing uses computer-aided design (CAD) data or 3D object scanners to deposit material layer-by-layer, into precise geometric shapes. Manufacturing an object with complex geometry by traditional methods is often difficult and requires numerous additional processes such as milling, processing, carving, modeling or other operations, increasing the cost of the implant. Although additive manufacturing is often also called "3D printing" or "rapid prototyping", each of these processes is actually a subset of additive manufacturing.

In one exemplary embodiment, a short cervical femoral endoprosthesis for hip articulation with application in orthopedics includes: a short body portion having a helicoid on the exterior wall, a collar, a neck, which are all aligned on the longitudinal axis of the prosthesis. The femoral endoprosthesis comprises a unitary component that is fabricated by additive manufacturing of the implant from a 3D model of the femoral component, which can follow the complexity of the shapes of the prosthesis.

According to one aspect of the present invention, an implantable cervical endoprosthesis includes a short prosthetic component that allows maintaining the anatomy of the coxofemoral articulation and its functions by maximizing the body's bone capital that remains in the area of implantation. The short cervical endoprosthesis presented in this invention preserves the anatomy of the femoral neck, the femoral neck length and the anatomy of the cervical trochanteric area.

The short cervical femoral endoprosthesis according to the invention, is less traumatic for the bone due to the helical spiral on the exterior of the body, which allow the insertion of the prosthesis by screwing it into the bone. The body of the prosthesis continues with a collar those edge is perpendicular to the axis of the prosthesis and aligned coaxially to the axis of the body. The collar continues with a tronconic neck on which the prosthesis head is later fixed. The prosthesis neck has a hexagonal orifice for the insertion of a dynamometric screwdriver so as to fix the prosthesis in place. The hexagonal orifice communicates inside the body with a cylindrical orifice of variable length and diameter, which further communicates with the arborization system of orifices that provide lateral feed with osteo-forming substances. The orifices with transversal variable diameter are displaced horizontally with an angle that varies between 90 and 180 degrees so as to introduce and fix the orthopedic cement or the osteo-stimulator substances, as needed.

In one embodiment, a proactive short cervical femoral endoprosthesis comprising a cylindrical central chamber such as a channel inside the prosthesis body contains in the middle a small threaded area in which a small, threaded cap can be screwed as needed. The cylindrical central channel of the body continues up to the body's tip having a smaller diameter than the anterior part but maintaining the same arborization system with transversal orifices of fixed diameters as in the first area of the endoprosthesis body.

According to the invention, a short implantable prosthesis can be used for all ages including children and young and active patients. Given a less invasive operative technique due to the short implant design, elderly patients suffering from osteoporosis may also benefit from short endoprosthesis. Using a short endoprosthesis preserves a large part of the bone as well. Also, the patients regain mobility shortly after the operation, with an early resumption of support on the operated leg because the primary stability of the endoprosthesis is given by cementation. Although the cementation is partial, the prosthesis is fixed in place and anchored through the arborization system or orifices filled with cement.

In case the endoprosthesis loosens (which could happen in 10, 15 years), the revision of the femoral stem with preservation of the femoral neck can be done with a classical prosthesis and not with a revision one, which would involve higher costs and a major surgical intervention.

Another embodiment disclosed herein is a proactive dental implant for supporting a dental prosthesis comprising of the same parts as the short-stem endoprosthesis and including a body, a collar and a neck, all having a common interior chamber with their main axis aligned with the longitudinal axis of the implant. Keeping the proportions of the design and all the parts comprising the implant, the dental implant is smaller and has a shorter collar. The dental implant also includes at least one thread located on at least a portion of the outer surface of the body.

Long implants can be placed in association with complex surgical procedures, such reconstruction and bone augmentation, which are associated with higher cost, increased treatment time and additional diseases associated with these types of techniques. Hence, there is need for a less invasive treatment option in areas of poor bone quantity and quality. Studies related to the survival rates of short implants, their design and prosthetic considerations have shown that comparable success rates can be achieved with short implants as those with long implants by decreasing the lateral forces to the prosthesis, eliminating cantilevers, increasing implant surface area and improving implant to abutment connection. Short implants can be considered as an effective treatment alternative in resorbed ridges, especially in dentistry, in order to avoid complex surgical procedures required to place long implants. With improvement in the implant surface geometry and the ability to control the substances required for fixing and healing the implant, there is an increase in the bone implant contact area which provides a good primary stability during osseo-integration.

These and other embodiments of the present invention will become readily apparent to those skilled in the art from the following detailed description of the preferred embodiments having reference to the attached figures, the invention not being limited to any particular preferred embodiment(s) disclosed.

BRIEF DESCRIPTION OF THE SEVERAL VIEWS OF THE DRAWINGS

Various examples of the present invention will be discussed with reference to the appended drawings. These drawings depict only illustrative examples of the invention and are not to be considered limiting of its scope.

FIG. 8 illustrates a 3D femoral model before (left) and after (right) the implant was mounted, and the cap was added.

FIG. 9 illustrates a close-up view of the 3D femoral model before (left) and after (right) the implant was mounted, and the cap was added.

DETAILED DESCRIPTION OF THE INVENTION

The preferred embodiments herein described are not intended to be exhaustive or to limit the invention to the precise form disclosed. They are chosen and described to explain the principles of the invention and its application and practical use to enable others skilled in the art to utilize its teachings.

Figure 1:
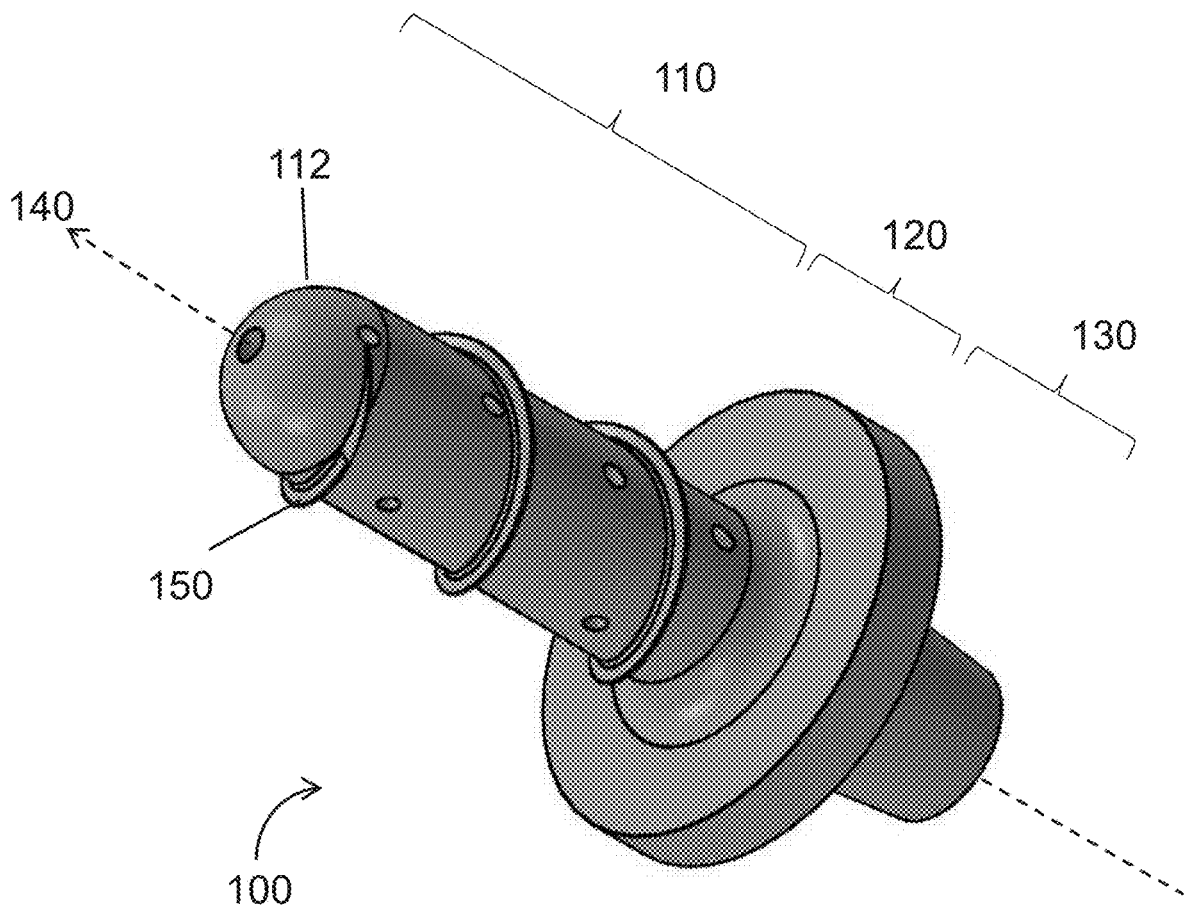
FIG. 1 is a perspective view of an illustrative short endoprosthesis according to the present invention.

FIG. 1 show a perspective of an illustrative endoprosthesis 100 having a cylindrical body part 110 with a distal end 112, a collar 120, a tronconic neck 130, and a longitudinal axis 140 therebetween. Preferably, the prosthesis is made of a biocompatible prosthesis material such as titanium alloys. The total length of the endoprosthesis 100 is 50-100 mm with a diameter of the body of 30-50 mm.

The cylindrical body 110 is provided with an helicoidal spire 150 on the exterior wall and continues up to the collar 120 located above the threaded portion of the outer surface and having the axis aligned with the prosthesis longitudinal axis 140, and then with an endoprosthesis neck 130 having a tronconic shape. The shape of a truncated cone of the neck is designed to hold later the prosthesis head.

Figure 2:
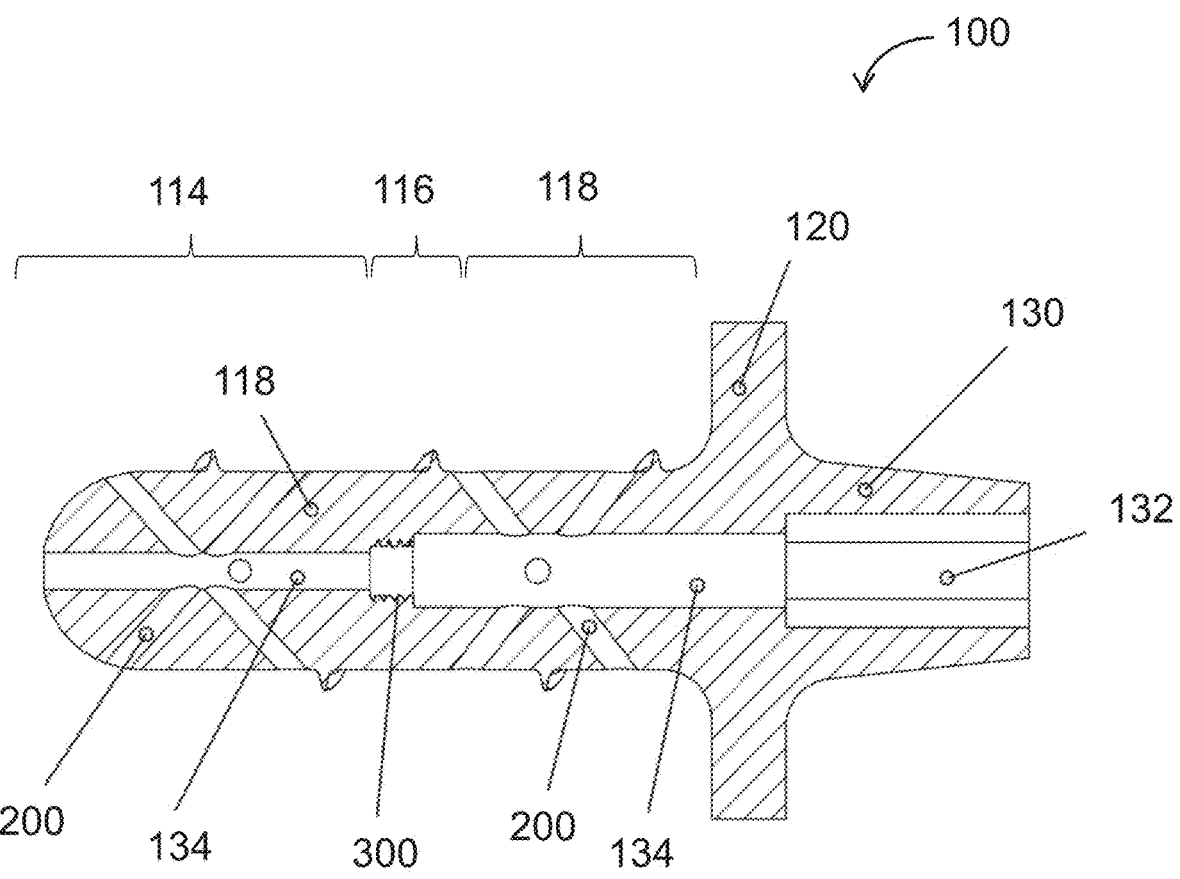
FIG. 2 is a section view taken along the longitudinal axis of FIG. 1

FIG. 2 is a longitudinal cross-section view along the endoprosthesis longitudinal axis 140 showing the interior designed architecture of the endoprosthesis hosting chambers with different operational functions, chambers that are connected and form an open channel. The neck 130 has a hexagonal orifice 132 for inserting a dynamometric screwdriver to secure the endoprosthesis in place. Orifice 132 will also house the prosthesis head (not shown here). Orifice 132 communicates with both the body and collar of the prosthesis, being aligned with them and aligned to the longitudinal axis 140.

The hexagonal orifice 132 of the prosthesis neck continues inside the body 110 and collar 120 with a cylindrical orifice 134 of variable shape, length and diameter, which communicates with an arborization-like system consisting of small, transverse holes 200 of variable diameter, offset horizontally with a variable angle between 90 and 180 degrees, having the role to feed the prosthesis with bone cement and bone substituents as needed, and further fix the endoprosthesis. Although the prosthesis is partially cemented, it will gain strength and stability from the anchorage provided by the cemented arborization system 200 and the internal orifice 134.

The cylindrical orifice consists in a distal part 114, a middle part 116 and a proximal part 118. The middle part 116 of the interior channel has a small threaded area 300 in which a small plug can be screwed when separation between chambers is required. The middle part 116 of the interior channel continues up to the distal end 112 with part 114, having a smaller diameter than the middle part 116 but retaining the same arborization-like system 200 with transversal orifices of fixed diameters as in the proximal part 118 of the endoprosthesis body. The middle part 116 of the interior channel continues up to the collar 120 with part 118, having a larger diameter than the middle part 116 to accommodate the syringe that deliver the bone cement and bone substituents, but retaining the same arborization-like system 200 with transversal orifices of fixed diameters as in the distal part 114 of the endoprosthesis body.

The interior channel, which is opened at both ends, has chambers and features that facilitate various operations, such as: feed the prosthesis with bone cement and bone substituents as needed, direct them through the arborization system of orifices, holds the plug that divide the chambers and fix the endoprosthesis with the help of the dynamometric screwdriver introduced in the hexagonal orifice of the neck 130. The hexagonal orifice of the neck is further used to house the prosthesis head.

Figure 3:
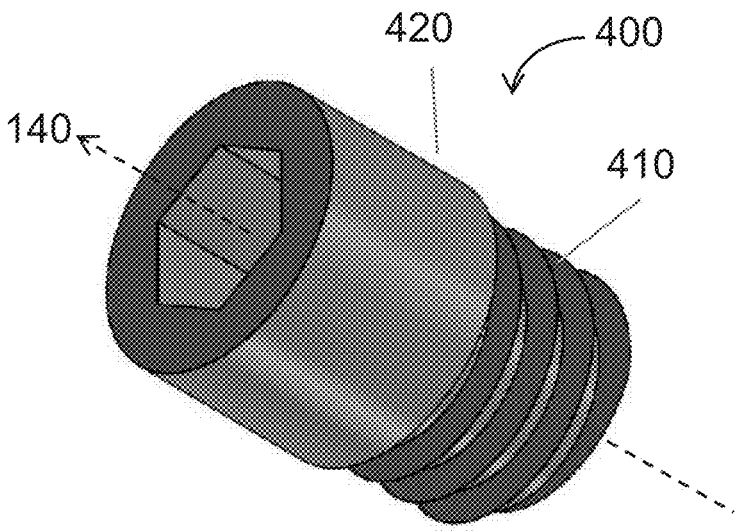
FIG. 3 is a perspective view of the small threaded plug.
Figure 4:
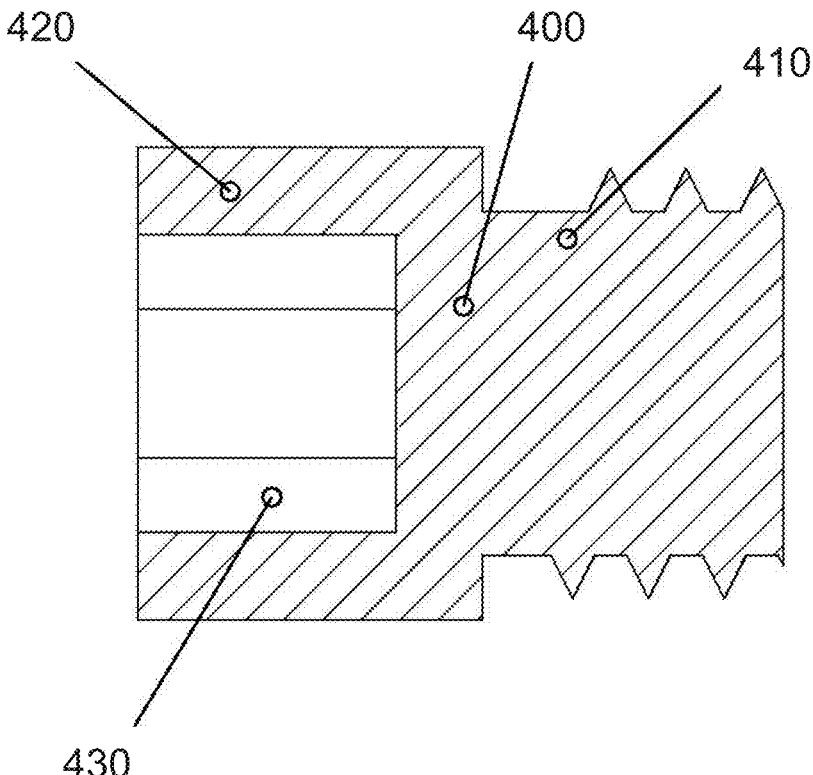
FIG. 4 is a section view taken along the longitudinal axis of FIG. 3

FIGS. 3-4 show a perspective view and a longitudinal cross section of the plug 400 that is hosted by the orifice 300. The plug has a threaded part 410 on the outside having the same length and pitch as the middle orifice 300 where it fits perfectly, and a cylindrical part 420 that has an inner hexagonal orifice 430 that is used for fixing in place or removing the plug as needed. The plug has a very important role in supplying or obstructing the flow of bone cement.

Figure 5:
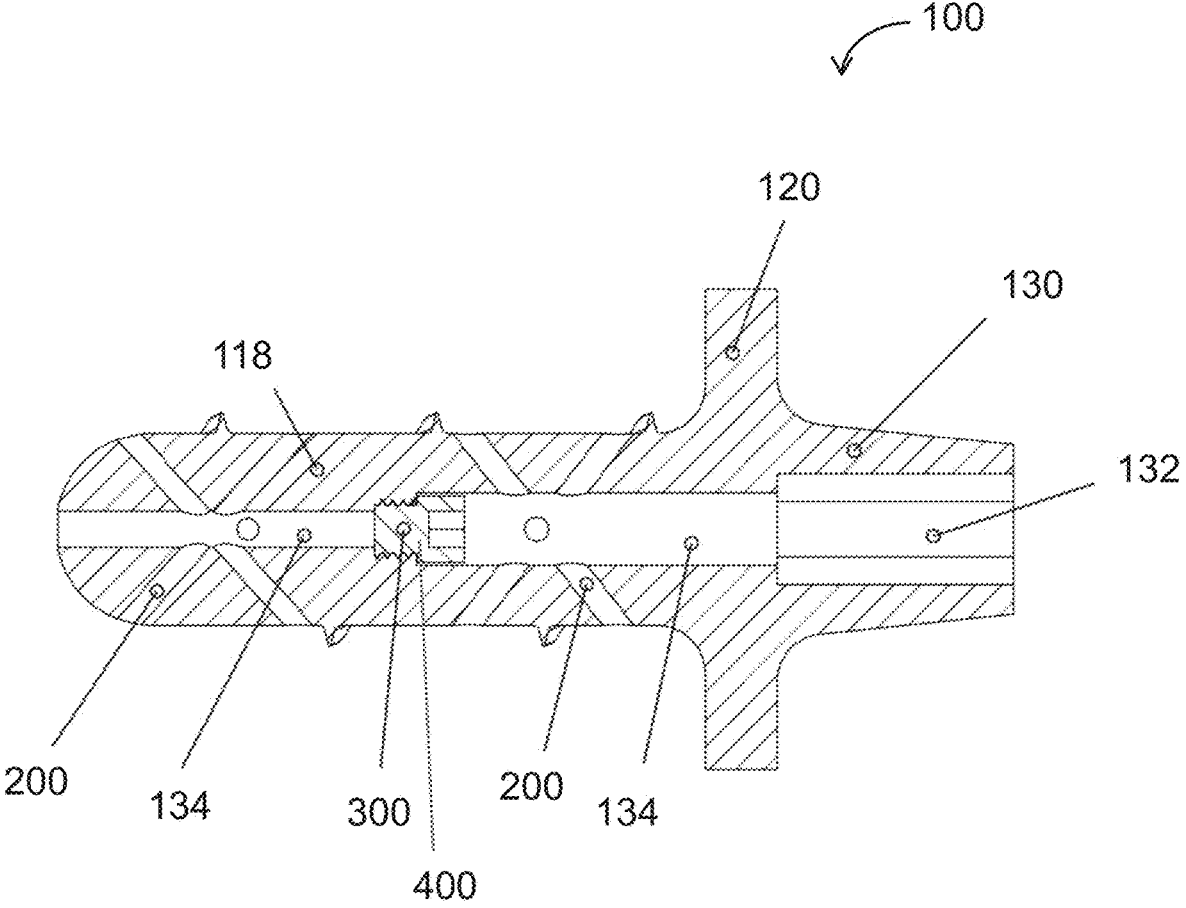
FIG. 5 is a section view taken along the longitudinal axis of FIG. 1 showing the plug inserted in the middle part of the body.

FIG. 5 shows the cross-sectional view of the prosthesis with the plug screwed in place in the threaded area 300, i.e. in the middle part 116 of the channel. Plug 400 divides the inner channel 134 of the body in two compartments, which gives the possibility of controlling the substances injected into each compartment and preventing their mixing. The plug 400 is threaded on the outside with a very fine pitch to fit perfectly into the middle orifice 300.

Figure 6:
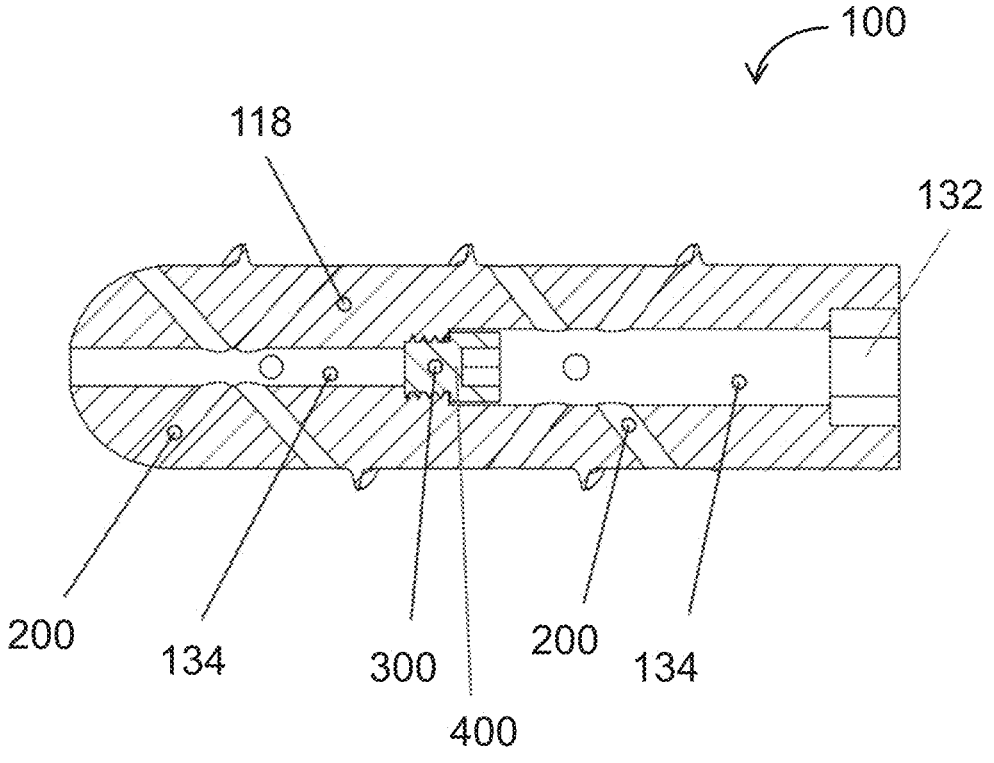
FIG. 6 is a section view taken along the longitudinal axis of FIG. 1 without collar for dental implant.
Figure 7:
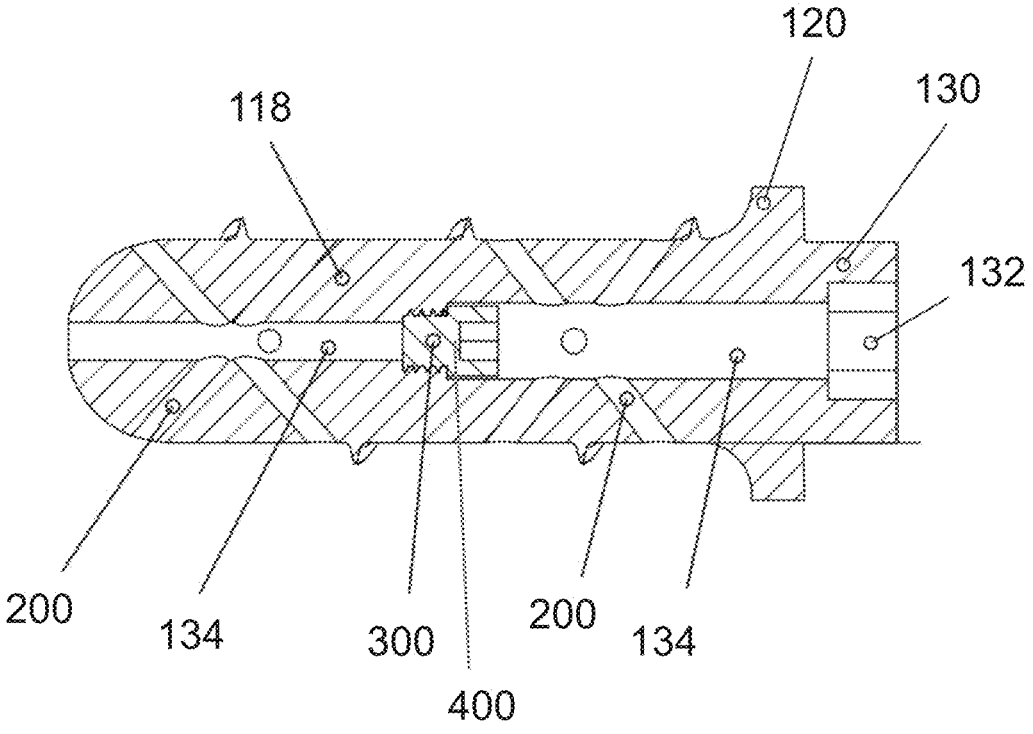
FIG. 7 is a section view taken along the longitudinal axis of FIG. 1 with a collar for dental implant.

FIGS. 6-7 show a longitudinal cross-section view along the longitudinal axis 140 of an implant that can be used in dentistry. The implant shown in FIG. 6 doesn't have a collar but consists of an interior designed architecture of the open channel similar to the short implant prosthesis presented in FIGS. 1-4. The proximal end has a hexagonal orifice 132 for inserting a dynamometric screwdriver to secure the endoprosthesis in place. Orifice 132 will also house the prosthesis head (not shown here). Orifice 132 communicates with both the body and collar of the prosthesis, being aligned with them and aligned to the longitudinal axis 140. FIG. 7 show a longitudinal cross-section view along the longitudinal axis 140 of an implant that can be used in dentistry having a collar 120.

FIGS. 8-9 illustrate a 3D femoral model before and after the implant was mounted, and the cap was added.

Figure 10:
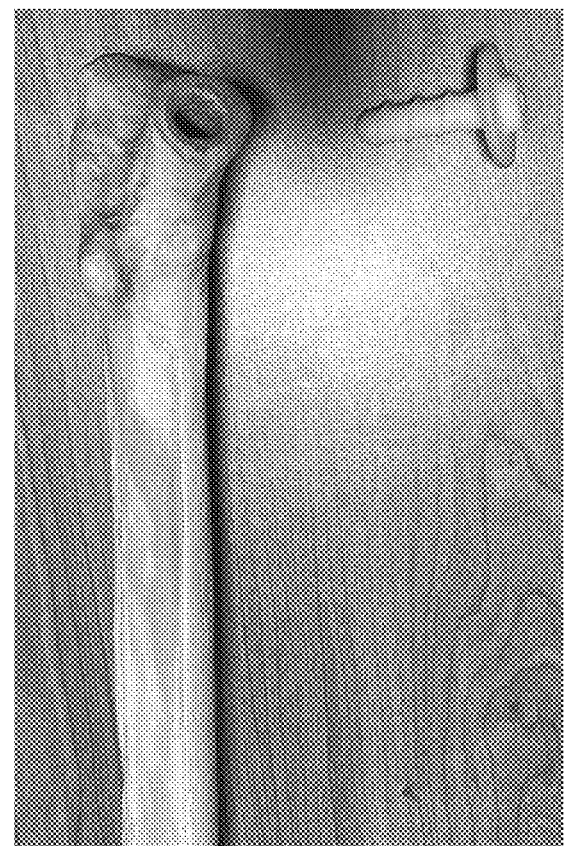
FIG. 10 illustrates an actual part of the femur bone and neck where the short endoprosthesis will be inserted.
Figure 11:
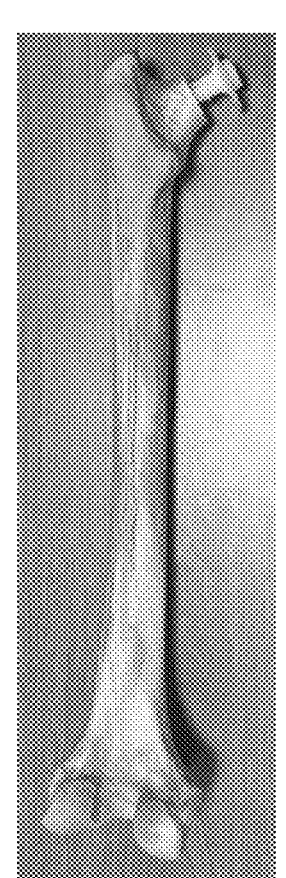
FIG. 11 illustrates an actual femur bone with the implant partially mounted.

FIG. 10 illustrates an actual part of the femur bone and neck where the short endoprosthesis will be inserted. The hole where the implant will be inserted is shown here only for illustrative purposes. In real life, the implant is actually screwed in the bone and does not leave the bone. FIG. 11 illustrates an actual femur bone with the implant partially mounted, also showing the size of the implant compared to the bone and the location of implantation.

The implanted prosthesis may be placed directly in contact with the bone surfaces for bony fixation of the implant.

Alternatively, bone cement may be introduced through the inner channel of the prosthesis body so that it hardens around and locks the prosthesis in place.

While both embodiments of this invention are illustrated using prosthesis with a unitary channel and provisional plug, the teaching of this invention can be incorporated into a single body component including the adjustable plug thereon. For example, the plug with the endoprosthesis of this invention has the possibility to compartmentalize and distribute through its network of channels and orifices various substances, such as: i) osteo-stimulating and bone forming substances or even liquid bone substitutes that reach the deficient areas in a controlled manner and thus increase the density of the bone mass immediately or in a short time and thus increase the secondary stability of the device and the survival of the implant over time in the prosthetic patient; ii) orthopedic cement with reduced viscosity that is able to go through these channels with the help of a piston syringe that can create a pressure high enough to allow the infiltration of the cement into the spongy bone tissue through the transverse orifices.

This cementation is used when the prosthesis is inserted for the first time the surgery is performed. In case of replacement, the cementation will take place after the injection of the bone-forming substances and after the channel has been obstructed with the plug to separate the compartments so that the substances do not mix in the bone mass.

The bio-compartmentation of the central channel is performed by creating an initial larger channel that continue beyond its half with a thinner central channel, which has at the entryway with a part threaded on the inside to allow for introducing a syringe that fits into the middle part of the channel and inject a bone forming substance whose role is to stimulate the peri-implant bone growth, especially on the tail tip in the trochanteric area. Later on, the middle part can be closed with a plug. The plug further prevents the orthopedic low viscosity cement from going into the final arborization-like system where the bone forming substance was initially introduced.

After closing the central channel of the body, the endoprosthesis (femoral stem) is further tightened with the dynamometric screwdriver, and then the orthopedic cement is injected, which will harden and thus it will "seal" the femoral prosthetic at the level of the femoral neck.

To this extent, the two zones were separated in one proximal, cemented cervical and one distal, trochanteric, osteo-stimulated with various osteo-forming substances that will remain intraosseous to perform their role over time and to achieve a lasting secondary fixation. So, the endoprosthesis (femoral stem) becomes proactive, both by the injected substance and by covering the tip with osteo-inductive substances such as hydroxyapatite. Over time, the prosthesis will become more stable and bond with the bone forming a joint body with the proximal femur. In time, the synergistic bone-metal action will take place where the metal takes over the tensions and rotational forces, and transfer them to the rest of the bone, just like any bone spans do with normal bone.

The endoprosthesis of this invention has the advantage of preserving as much bone capital as possible and maintains the anatomy of the hip and implicitly its functions. The fixation system still remains press-fit with the help of screwing the part into the cervical spongy bone tissue (not forcing, or axial compression). By infiltrating the proximal area of the endoprosthesis with an integrative material such as hydroxyapatite, the secondary attachment of the endoprosthesis is achieved, and by introducing the orthopedic cement, the axial stability of the endoprosthesis is improved as well as the final fixation. The osteo-forming substance injected in the distal zone of the prosthesis is intended to increase the bone mass, thus increasing the stability of the bone projection but also preventing hip fractures, such as femoral neck fractures, pertrochanteric fractures or subtrochanteric fractures. The osteo-forming substance could be a gel obtained from a mechanical mixture of hydroxyapatite with collagen, in which doxycycline was incorporated in proportions that vary from case to case.

The advantages of the endoprosthesis according to the invention consist in achieving a more stable mounting and ease of implantation, as well as accelerating functional recovery, with maximum preservation of the bone capital in the implantation area. The fact that a multitude of substances can be introduced through the inner channel and arborization system makes it very useful for most patients without osteoporosis.

With this type of endoprosthesis, is it possible for the patient to regain mobility starting the day after the surgery thanks to minimally invasive techniques that create a new hip joint without muscle sacrifice and with minimal bleeding, while the procedure for cementing the endoprosthesis allows an early resumption of support on the operated leg.

The endoprosthesis mounting technique consists of several steps as follows. After the mini-invasive hip intervention and the dislocation of the femoral head in the wound, the subcapital osteotomy is performed with the removal of the femoral head. The acetabular cavity is then prepared in the same way as for any prosthesis surgery. The diameter of the femoral neck is measured on the sectional plane and its center is marked. A guided metal pin is inserted in the middle of the femoral neck (guide pin) which is perpendicular to the plane of the transom of the femoral neck, which will allow the perfect application of the collar of the prosthesis after the final screwing on the resection transom. The endoprosthesis is permanently implanted by screwing with the help of a dynamometric screwdriver (up to a couple of forces that will prevent unscrewing regardless of the forces applied to the prosthetic hip) and until fits perfectly on the resection transom, without leaving any space between the collar of the prosthesis and the bone transom. By inserting and screwing in place the endoprosthesis, the spongy cervico-trochanteric tissue of the bone in the vicinity of the prosthesis is compacted, which increase the local bone density and better support the endoprosthesis thread. A metal syringe having an external thread is inserted and fixed into the central threaded area of the channel in the center of the prosthesis and the osteo-forming cement is injected under pressure. Then, unscrew the needle and immediately insert and screw in place an obturating plug. With the help of a syringe, the orthopedic cement is inserted through the inner channel of the prosthesis, the cement coming out through the transverse orifices, filling the bone alveoli in the vicinity of the endoprosthesis. By strengthening the endoprosthesis using the dynamometric screwdriver, the cement will come out through the grooves or protrusions of the prosthesis behind the collar and will further stabilize the prosthesis in the femoral neck. The only possibility of extracting the prothesis after the insertion of prothesis and strengthening of the bone is the osteotomy of the femoral neck. The head of the endoprosthesis (metal or ceramic) with various diameters to fit on the truncated neck is fixed into the tronconic neck of the endoprosthesis. Finally, the dislocation of the prosthesis is reduced and the stability, degree of mobility and resistance to forced movements are checked.

The tridimensional digital model of the endoprosthesis was obtained by computer aided designing, its design being verified by means of the specific techniques of aided analysis through the finite element method, by varying its characteristic parameters, such as angles of the screw and thread geometry, thread step, thread step depth, number of transversal orifices for introducing the orthopedic cement, and by taking into account the surface of the medullary canal and of the bony trabecular tissue.

This implant is not a simple screw, it has certain designed features that will strengthen the structure of the femoral neck preserved in its entirety by screwing it in and applying it firmly through its collar fixed on the resection area of the femoral neck. This implanted prosthesis is a mixed, cemented and or non-cemented, proactive prosthesis meaning that bone forming substances with or without antibiotic can be injected and delivered through inner channels in order to harden the bone network around the prosthesis and increase the stability, i.e., the secondary fixation. This secondary fixation is essential since it will maintain the stability of the prosthesis in the long term. The primary fixation of the implant is carried out in two ways, by screwing and cementation. By screwing, uncemented implant, to gather and compact the cervico-trochanterian spongy tissue in order to increase its bone density. Through this screwing, the main body of the implant is fixed by means of the collar siting on the resection area of the femoral neck. Through the perfect application of the prosthesis collar on the resection area, the forces at the level of the femoral neck will dissipate, especially the forces that tend to increase or decrease the cervico-diaphyseal angle or the anteversion of the femoral neck. This manner of immediate transfer of the forces to the bone, relieving the role of the prosthesis in the final support, is beneficial in stimulating the bone and thus preventing bone resorption due to a lack of mechanical stimulation of the remaining bone. This phenomenon is called "stress shielding" in the literature. However, because it is not enough to apply the collar on the bone transom and because there is a risk of its loosening or migration during the patient's mobilization the very next day or even immediately postoperatively, this invention introduces a second means of primary fixation, namely: cementing only in the proximal portion, i.e. in the femoral neck, which will lead to a stiffening of the prosthesis and a strengthening of the femoral neck. In this way, all forces including torsional ones are transmitted through the orthopedic cement to the bone adjacent to the prosthesis, namely the femoral neck and further to the trochanter bone and the femoral diaphysis. The cementing of the prosthesis is only partial, because the interest is not to fill the bone with cement, but only to "seal" the prosthesis in the femoral neck, keeping the rest of the bone viable and maintaining a permanent stimulation of it through the forces applied at the level of the proximal femur. In this way, the main role of the bone to take over and transfer the forces is preserved and thus bone resorption is prevented due to the presence of an implant in the bone to take over the forces.

The present invention has been illustrated and described with particularity in terms of preferred embodiments. Nevertheless, it should be understood that no limitation of the scope of the invention is intended thereby. The scope of the invention is defined by the claims appended hereto. It should also be understood that variations of the particular embodiments described herein incorporating the principles of the present invention will occur to those of ordinary skill in the art and yet be within the Scope of the appended claims.

REFERENCES

[1] W. E. Lorensen, H. E. Cline, "Marching Cubes: A high resolution 3D surface reconstruction algorithm", *SIG-GRAPH '87 Proceedings of the* 14*th annual conference on Computer graphics and interactive techniques,* 1987, USA

[2] Y. Heng, L. Gu, "GPU-based volume rendering for medical image visualization", *Proceedings of the IEEE Engineering in Medicine and Biology* 27*th Annual Conference,* 2005, Shanghai, China

[3] S. Martin, H. Shen, P. McCormick, "Load-balanced isosurfacing on multi-GPU clusters", *Eurographics Symposium on Parallel Graphics and Visualization,* 2010

[4] H. R. Nagel, "GPU optimized Marching Cubes algorithm for handling very large, temporal datasets", *CiteSeerX—Scientific Literature Digital Library and Search Engine,* 2010

[5] B. Preim, D. Bratz, *Visualization in medicine.* Elsevier, Morgan Kaufmann Publishers, 2007, USA "NVIDIA CUDA C—Programming guide". Version 3.2, 2010, NVIDIA Corporation

[7] Orban, H., Bunea, D., Moldovan, L., Antoniac, I., Gheorghiu, D., Semenescu, A.: Componenta femurala pentru proteza totala de sold, Romanian Patent RO 117890 B, State Office for Inventions and Trademarks, 30 Sep. 2002.

[8] Gelalis, L., D., Xenakis, T., A., Hantes, M., Vartziotis, K., Soucacos. P., N.: Three-dimensional computerized selection of hip prostheses in patients with congenital dislocated hips, Journal of Orthopedics, 2001

[9] Laurian, Tiberiu: Contributii privind fenomenele tribologice în protezele de sold—Teza de doctorat, UPB, 2007.

[10] G N Duda 1, M Heller, J Albinger, O Schulz, E Schneider, L Claes: Influence of muscle forces on femural strain distribution, *Journal of Biomechanics* 31, 1998, 841-6

[11] Brodke, D., S., Gollogly, S., Alexander, Mohr, R., Nguyen, B., K., Dailey, A., T., Bachus, K.: Dynamic cervical plates: biomechanical evaluation of load sharing and stiffness. Spine, Vol. 26, Issue 12, 2001.

[12] Gheorghe, I., Gh., Palade D., D., Ciobota, N., D., Pacioga, A.: Microtehnologii avansate prin prototipare rapida utilizând sinterizarea directa cu laser, Bucuresti, Editura CEFIN, 2010.

[13] ***: ISO 7206-4:2002: Implants for surgery-Partial and total hip prostheses, Part 4-Determination of endurance properties of stemmed femoral components.

[14] ***: ISO 7206-8:2002: Implants for surgery-Partial and total hip prostheses, Part 8-Endurance performances of stemmed femoral components.

[15] ***: Legea nr. 176 din 18 octombrie 2000 privind dispozitivele medicale, Publicata în Monitorul Oficial al României nr. 544.

[16] ***: SolidWorks—3D CAD Design Software, http://www.solidworks.com/.

[17] Demian, C.: Cercetari privind comportarea materialelor destinate implantarii osoase conform normelor europene de calitate, Teza de doctorat, Politehnica Timisoara, 2006.

[18] Günay, M.: Three-dimensional Bone Geometry Reconstruction from X-ray Images Using Hierarchical Free-form Deformation and Non-linear Optimization, in Mechanical Engineering Department Carnegie Mellon University, Pittsburgh, Pennsylvania, 2003.

[19] Hua, J., Walker, P., S., Meswania, J., Muirhead-Allwood, S., K., Catterall, T.: The role of 3D Image Reconstruction and Rapid Prototyping Models in Total Hip Arthroplasty, http://www.materialise.com/materialise/view/en/422029.

[20] Kurazume, R., Nakamura, K., Okada, T.: 3D reconstruction of a femoral shape using a parametric model and two 2D fluoroscopic images—International Conference of Robotics and Automation, 2007.

[21] Pacioga, A., Comsa, St., Musat, C.: Selection of biomaterials for orthopedic applications using the pondered proprieties method, Romanian Review Precision Mechanics, Optics and Mechatronics nr. 36/2009, ISSN1584-5982 and the International Conference 6$^{th}$ Workshop on European Scientific and Industrial Collaboration on Promoting Advanced Technologies in manufacturing WESIC '08.

[22] Pacioga, A., Palade, D., D., Comsa, St.: Computational Simulation of Bone—Personalized Hip Prosthesis Assembly, U.P.B. Scientific Bulletin, Series D, Vol. 73, Issue 2, 2011 ISSN 14542358.

[23] Pacioga, A., Palade, D., D., Comsa, St.: Joint Motion Area Related to Prosthesis Component Position In Total Hip Arthroplasty, Romanian Review Precision Mechanics, Optics and Mechatronics nr. 38/2010, ISSN 1584-5982.

[24] Pacioga, A.: Stadiul actual si tendinte în modelarea si fabricarea asistate de calculator a implanturilor osoase, Raport stiinific de doctorat nr. 2, prezentat în sedinta de catedra, 6 Nov. 2009.

[25] Pacioga, A.: Forme constructive si materiale utilizate în artroplastia de sold, Studiu individual comparativ, prezentat în fata comisiei de evaluare, 25 Jun. 2008.

[26] Bourne R, Rorabeck C. Soft tissue balancing, the hip. J Arthroplasty 2002; 17 (4 Suppl. 1): 17-22.

[27] Suh K T, Kang J H, Roh H L, Moon K P, Kim H J. True femoral anteversion during primary total hip arthroplasty. Use of postoperative computed tomography-based sections. J Arthroplasty 2006; 21:599-605.

[28] Olivecrona H, Weidenhielm L, Olivecrona L, et al. A new CT method for measuring cup orientation after total hip arthroplasty, a study of 10 patients. Acta Orthop Scand 2004; 75:252-60.

[29] Sariali E, Mouttet A, Pasquier G, Durante E. Three-dimensional hip anatomy in osteoarthritis, analysis of the femoral offset. J Arthroplasty 2009; 24:990-7.

[30] Charles M, Bourne R, Davey R, Greenwald S, Morrey B, Rorabeck C. Soft tissue balancing of the hip, the role of femoral offset restoration. J Bone Joint Surg (Am) 2004; 86:1078-88.

[31] Nishii T, Sugano N, Miki H, Koyama T, Takao M, Yoshikawa H. Influence of component positions on dislocation Computed tomographic evaluations in a consecutive series of total hip arthroplasty. J Arthroplasty 2004; 19:162-6.

[32] Noble P C, Sugano N, Johnston J, Thompson M, Conditt M, Engh C, et al. Computer simulation: how can it help the surgeon to optimize implant position. Clin Orthop 2003; 417:242-52.

[33] Seel M J, Hafez M A, Eckman K, Jramaz B, Davidson D, Di Gioia A M. Three-dimensional planning and virtual radiographs in revision total hip arthroplasty for instability. Clin Orthop 2006; 442:35-8.

[34] Flecher X, Argenson J N, Paratte S, Ryembault E, Aubaniac J M. Tiges fémorales sur mesure non cimentées pour séquelle de dysplasie et luxation congénitale de hanche. Rev Chir Orthop 2006; 92:332-42.

[35] Argenson J N, Ryembault E, Flecher X, Paratte S, Aubaniac J M. Three-dimensional anatomy of the hip in osteoarthrosis after developmental dysplasia. J Bone Joint Surg (Br) 2005; 87:1192-6.

[36] Murray D W. The definition and measurement of acetabular orientation. J Bone Joint Surg (Br) 1993; 75:228-32.

[37] Noble P C, Alexander J W, Lindhal L J, Yew D T, Granberry W M, Tullos H S. The anatomic basis of the femoral component design. Clin Orthop 1988; 235:148-62.

[38] Rubin P J, Leyvraz P F, Aubaniac J M, Argenson J N, Esteve P, Deroguin B. The morphology of the proximal femur a three dimensional radiographic analysis. J Bone Joint Surg 1992; 74:28-32.

[39] Eggli S, Pisan M, Muller M E. The value of preoperative planning for total hip arthroplasty. J Bone Joint Surg 1998; 80:382-90.

[40] De Thomasson E, Mazel C, Guingand O, Terracher R. Etude critique des résultats de la planification préopératoire sur l'anatomie de la hanche prothésée. Rev Chir Orthop 2002; 88:229-35.

[41] Mc Grory B, Morrey B, Cahalan T, An K, Cabanela M, Effect of femoral offset on range of motion and abductor muscle strength after total hip arthroplasty. J Bone Joint Surg 1995; 77:865-9.

[42] Asayama I, Chamnongkich S, Simpson K, Kinsey T, Mahoney O. Reconstructed hip joint position and abductor muscle strength after total hip arthroplasty. J Arthropasty 2005; 20:414-20.

[43] Noble P C, Kamaric E, Sugano N, Matsubara M, Harada Y, Ohzono K, et al. Three-dimensional shape of the dysplasic femur: implications for THR. Clin Orthop 2003; 417:27-34.

[44] Argenson J N, Flecher X, Paratte S, Aubaniac J M. Anatomy of the dysplasic hip and consequences for total hip arthroplasty. Clin Orthop 2007; 465:40-5.

[45] Massin P, Geais L, Astoin E, Simondi M, Lavaste F. The anatomic basis for the concept of lateralized femoral stem A frontal plane radiographic study of the proximal femur. J Arthroplasty 2000; 15:93-101.

[46] Ranawat C S, Rao R R, Rodriguez J A, Bhende H S. Correction of limb-length inequality during total hip arthroplasty. J Arthroplasty 2001; 16:715-20.

[47] Jasty M, Webster W, Harris W. Management of limb length inequality during total hip replacement. Clin Orthop 1996; 333:165-71.

[48] Maloney W J, Keeney J A. Leg length discrepancy after total hip arthroplasty. J Arthroplasty 2006; 21:108-10.

[49] Konyves A, Bannister G C. The importance of leg length discrepancy after total hip arthroplasty. J Bone Joint Surg 2005; 87:155-7.

[50] Krishnan S, Carrington R, Mohiyaddin S, Garlick N. Common misconceptions of the normal hip joint, relations on pelvic radiographs. J Arthroplasty 2006; 21:409-12.

[51] Adrian Pacioga, Doru D. Palade, Stanca Comsa, Joint motion area related to prosthesis component position in total hip arthroplasty. The Romanian Review Precision Mechanics,

[52] Neha Jain, Manisha Gulati, Meenu Garg, and Chetan Pathak, Short Implants: New Horizon in Implant Dentistry, J Clin Diagn Res. 2016 September; 10 (9): ZE14-ZE17. doi: 10.7860/JCDR/2016/21838.8550

What is claimed is:

1. A proactive short cervical femoral endoprosthesis comprising, a cylindrical body part, said body comprising of an interior chamber, an outer surface of said body is provided with an helicoidal spire for engaging bone and an inner surface of said body delimiting the interior chamber, said chamber has variable lengths, diameters and shapes and communicates with an arborization system of transversal variable diameter orifices; said chamber has a middle treaded portion for the insertion of a syringe that delivers orthopedic cement and osteo-stimulating substances through the prosthesis;

said orifices therethrough extending from the inner chamber to the exterior of said body, said orifices are displaced horizontally with variable angles between 90 and 180 degrees so as to distribute the orthopedic cement and the osteo-stimulating substances; at least a portion of said orifice being, in transverse cross-section circular and communicating with the inner chamber of said body;

a collar located above a threaded portion of the outer surface of said body, said collar having a cylindrical chamber communicating with the interior chamber of the said body and having the main axis aligned with the longitudinal axis of said body;

a neck with a tronconic shape on which a prosthesis cap is fixed, said neck has an orifice of hexagonal shape for introducing a dynamometric screwdriver so as to fix the endoprosthesis, said orifice is axially aligned with the longitudinal axis of the cylindrical body and collar and communicate with both said body and collar for introduction of orthopedic cement and osteo-stimulating substances; said orifice being configured to attach a prosthesis head.

2. The proactive short cervical femoral endoprosthesis of claim 1 wherein the entire implant is made of biocompatible metal alloy.

* * * * *